United States Patent [19]

Mueller et al.

[11] Patent Number: 5,792,435
[45] Date of Patent: Aug. 11, 1998

[54] VAPOR PHASE DECONTAMINANT ISOLATOR APPARATUS WITH INTEGRAL VAPOR PHASE DECONTAMINANT GENERATOR SYSTEM

[75] Inventors: Wolfgang Mueller, Erie, Pa.; Udo J. Werner, Tettnang, Germany

[73] Assignee: Steris Corporation, Mentor, Ohio

[21] Appl. No.: 835,769

[22] Filed: Apr. 8, 1997

[51] Int. Cl.[6] .................................................. A61L 9/00
[52] U.S. Cl. ........................ 422/292; 422/300; 422/302; 422/304; 422/306; 422/308
[58] Field of Search ........................... 422/292, 300, 422/302, 304, 306, 308, 297

[56] References Cited

U.S. PATENT DOCUMENTS

| | | | |
|---|---|---|---|
| 5,053,196 | 10/1991 | Ide et al. | 422/28 |
| 5,152,968 | 10/1992 | Foti et al. | 422/304 |
| 5,173,258 | 12/1992 | Childers | 422/27 |
| 5,525,295 | 6/1996 | Pflug et al. | 422/27 |
| 5,639,432 | 6/1997 | Carlson | 422/302 |

Primary Examiner—Krisanne Thornton
Attorney, Agent, or Firm—Fay, Sharpe, Beall, Fagan, Minnich & McKee

[57] ABSTRACT

A flow-through vapor phase decontamination apparatus includes at least one isolator unit (14) defining an isolation chamber (16) that receives a load (L) for decontamination. The apparatus includes a vapor phase decontaminant generation system (20) integrally connected to the at least one isolator unit (14). The vapor phase decontaminant generator system (20) includes one or more vaporizers (22) that inject a combination of a carrier gas and a vaporized decontaminant such as $H_2O_2$ into the isolation chamber (16). A blower (24) recirculates the carrier gas through the one or more vaporizers (22) for replenishment of the decontaminant vapor. Alternatively, an automated filling system (70a–70c) is provided within the isolation chamber (16) for aseptic filling of containers (C). A conveyor system (68) transports the containers (C) into and out of the isolation chamber (16). The decontamination apparatus includes an electronic control system (26) for controlling decontamination operations.

13 Claims, 3 Drawing Sheets

VAPOR PHASE DECONTAMINANT ISOLATOR APPARATUS WITH INTEGRAL VAPOR PHASE DECONTAMINANT GENERATOR SYSTEM

BACKGROUND OF THE INVENTION

The present invention relates to the decontamination arts. It finds particular application in conjunction with flow-through decontamination systems that utilize vapor phase decontaminants such as vapor phase hydrogen peroxide and vapor phase peracetic acid and will be described with particular reference thereto. However, it is to be appreciated that the invention may find further application with other gaseous decontamination systems.

Vapor phase decontamination is a well known method for decontaminating medical, pharmaceutical, and biological instruments, equipment, and products. Further, reusable enclosures employed in medical, pharmaceutical, and biological applications such as glove boxes and incubators are generally decontaminated before each use using vapor phase decontamination methods.

Different methods have been developed for delivering a vapor phase decontaminant to an enclosure for sterilizing the enclosure and/or a load contained in the enclosure, e.g., medical instruments and devices, and pharmaceutical containers and products. Of course, the particular vapor phase decontaminant generation/delivery system employed depends upon the application. In general, however, two main vapor phase decontamination methods are utilized. In one option, the "deep vacuum" approach, a deep vacuum is used to pull liquid decontaminant into a heated vaporizer. Once vaporized, the decontaminant is propelled by its vapor pressure into an evacuated and sealed chamber to decontaminate a load contained therein. In another option, the "flow-though" approach, vaporized decontaminant is mixed with a flow of carrier gas that serves to deliver the decontaminant vapor into, through, and out of the chamber. While in the chamber, the vapor phase decontaminant acts upon he load to decontaminate it. The chamber may be maintained at a slightly negative or a slightly positive pressure relative to ambient conditions.

The present invention is primarily concerned with the latter, flow-through vapor phase decontamination systems, although it may also find application in vacuum systems. Heretofore, flow-through decontamination systems have included a rigid-walled enclosure or a flexible-walled tent-type enclosure (collectively referred to as isolators) to define an isolation chamber into which a load to be decontaminated is placed. A separate vapor phase decontaminant generator apparatus has been positioned adjacent and fluidically connected to the isolator to communicate a vapor phase decontaminant into the isolation chamber along with the carrier gas.

In addition to simple isolators that merely define an isolation chamber for a load, complex isolators, usually rigid-walled, have been developed for large-scale, complex decontamination operations. These larger isolators have been developed as alternatives to class 1000 clean rooms and the like. More particularly, in many applications, isolators provide economic advantages as well as safety and process control advantages over clean rooms. In general, enclosing the manufacturing/laboratory operations in an isolator minimizes opportunity for operator error and accidental contamination. These isolators include automated or semi-automated filling and other processing systems for carrying out sterile operations within the isolator. Operations that are not automatically carried out within the isolation chamber are carried out by an operator through a glove box or similar sterile access device.

One deficiency associated with known isolators has been the need to connect the isolators to separate vapor phase decontaminant generators. The use of separate vapor phase decontaminant generators has proven to be inconvenient. The separate decontaminant vapor generators have increased the footprint of the decontamination system overall. Further, it has been found difficult to tailor the capacity of the separate decontaminant vapor generator to customized isolator systems. Often, the separate isolator systems are not capable of continuous operation which is preferred for increased productivity. Also, the use of a separate decontaminant vapor generator prevents the consolidation of the isolator controls with the control system of the vapor generator. Because of the foregoing deficiencies associated with known isolator decontamination systems, the capacity and abilities of prior isolator systems have been limited.

The present invention provides a new and improved decontamination apparatus for overcoming the above-referenced problems and others.

SUMMARY OF THE INVENTION

In accordance with the present invention, a decontamination apparatus includes a chassis. At least one isolator unit is connected to and supported by the chassis. The isolator unit includes a generally hollow isolation chamber defined therein. A vapor phase decontaminant generation system is also connected to and supported by the chassis, integrally with the isolator unit. The integral vapor phase decontaminant generation system includes at least one vaporizer for vaporizing aqueous decontaminant. The integral vapor phase decontaminant generation system also includes a blower for communicating a carrier gas from the isolation chamber to the vaporizer for combination with a vapor phase decontaminant. The blower also communicates the combined carrier gas and vapor phase decontaminant to the isolation chamber. The decontaminant vapor generation system also includes an electronic control system with at least one central processing unit for controlling the operation of the vaporizer.

One advantage of the present invention is that it integrates a vapor phase decontaminant generator into a vapor phase decontaminant isolator.

Another advantage of the present invention is that it provides a continuous operation vapor phase decontaminant generator integrated into a vapor phase decontamination isolator.

Still another advantage of the present invention is that it provides a modular isolator system including plural isolator units and plural decontaminant vaporizers integrated into a single vapor phase decontamination apparatus.

Yet another advantage of the present invention is the provision of a vapor phase decontamination isolator with an integrated vapor phase decontaminant generator which is connected to a permanent heating, ventilation, and air-conditioning system for continuous conditioning of the vapor phase decontaminant carrier gas.

A further advantage of the present invention is that it provides a decontamination apparatus including an isolation chamber with an automated sterile processing system and an integral vapor phase decontaminant generator system.

Still other advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components. The drawings are only for purposes of illustrating preferred embodiments and are not to be construed as limiting the invention.

DETAILED DESCRIPTION OF THE PREFERRED EMBODIMENTS

The term "decontamination" shall be understood to include sterilization, disinfection, and sanitization. The preferred decontaminant utilized in conjunction with the decontamination apparatus of the present invention is vapor phase hydrogen peroxide generated from 30–35% by weight aqueous hydrogen peroxide solution ($H_2O_2$). Alternatively, vapor phase peracetic acid or any other suitable vapor phase decontaminant is utilized. The carrier gas is preferably air, although any gas that is non-reactive to the utilized vapor phase decontaminant and the processed material can be utilized. For purposes of describing the preferred embodiments, the carrier gas and the decontaminant discussed will be air and vapor phase $H_2O_2$, respectively.

Figure 1:
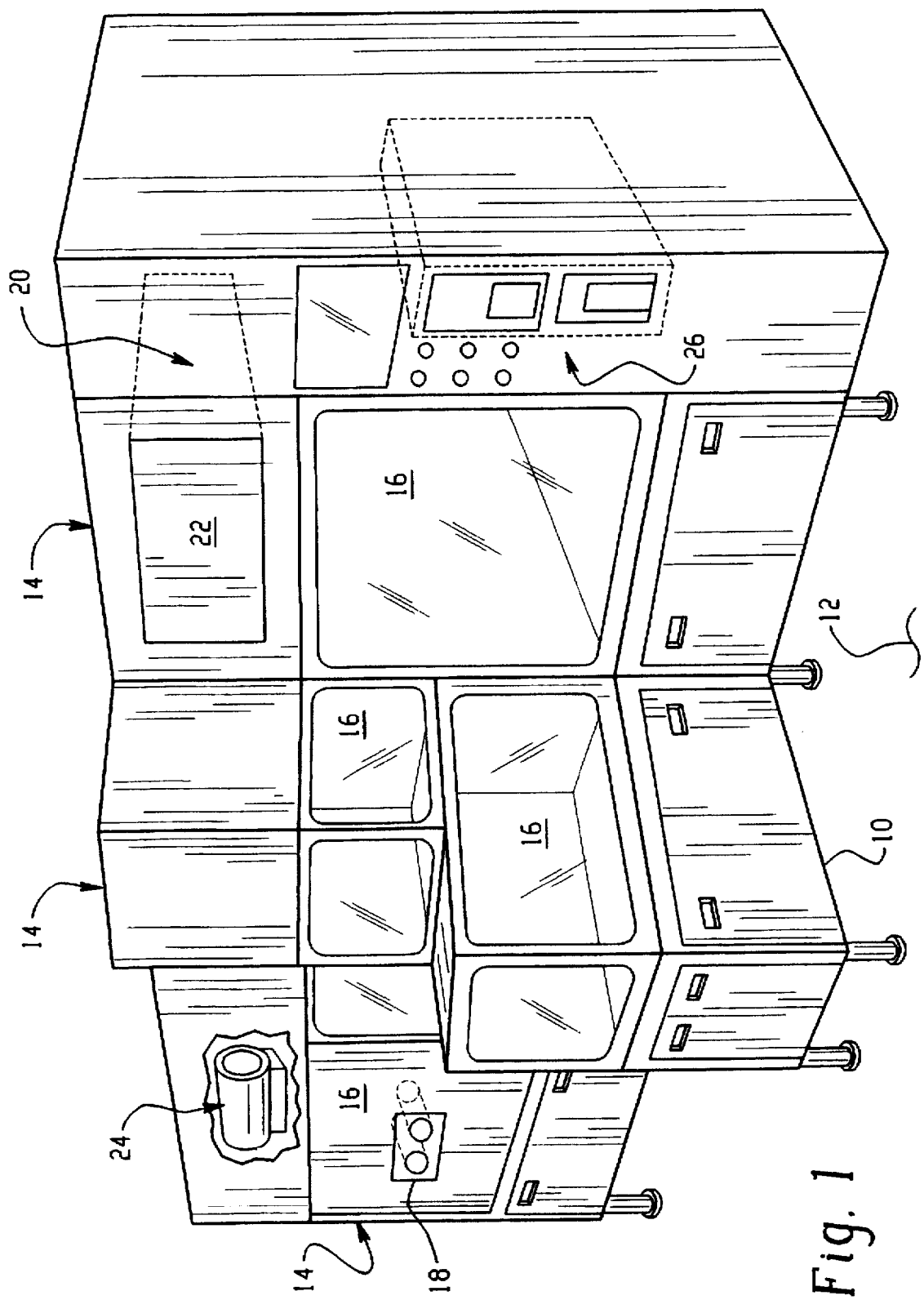
FIG. 1 is a perspective illustration of a decontamination apparatus in accordance with the present invention.

Referring more particularly to FIG. 1, an apparatus for flow-through vapor phase decontamination of articles includes a frame or chassis 10 for supporting the apparatus above a support surface 12 such as a floor. The decontamination apparatus includes at least one generally hollow isolator unit 14 supported on the chassis 10. Together, the one or more isolator units 14 define a generally hollow isolation chamber 16 which receives a load for decontamination of course, the isolation chamber 16 can be provided by a single isolator unit 14. The modular isolator units 14 are rigid-walled, constructed of a metal such as stainless steel and glass for operator visual access. Further, one or more glove boxes 18 or the like are conveniently provided, as necessary, for operator manipulation of the load within the isolation chamber 16.

At least one vapor phase decontaminant generator system 20 is connected to and supported by the chassis 10 to be integrally connected to the one or more isolator units 14 defining the isolation chamber 16. The decontaminant vapor generator system 20 includes at least one vaporizer 22 which produces a vapor phase decontaminant such as vapor phase $H_2O_2$ and entrains the vapor into a carrier gas such as air which is circulated into the isolation chamber 16 to decontaminate the load. For circulation of the carrier gas, a blower 24 is provided. The blower 24 continuously withdraws air from the isolation chamber 16 and circulates the air to the vaporizer 22 for replenishment of the vapor phase decontaminant into the carrier gas. The generator system 20 also includes an electronic control system 26 which controls the vaporizer 20 and provides for operator input and output of data such as decontamination process parameters.

Figure 2:
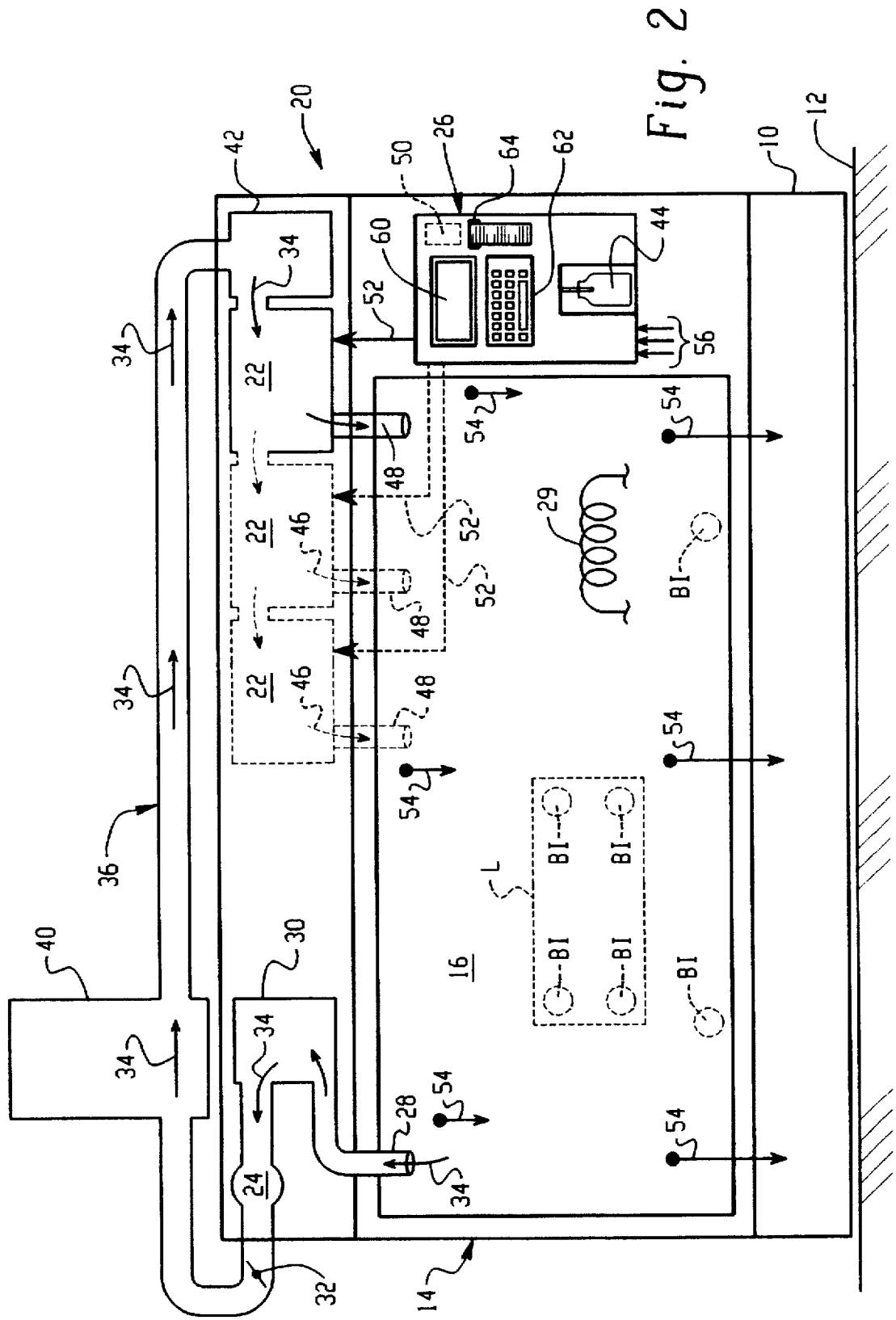
FIG. 2 is a diagrammatic illustration of the decontamination apparatus of FIG. 1; and, FIG. 3 is a diagrammatic illustration of a decontamination apparatus in accordance with a second embodiment of the present invention.

Referring now to FIG. 2, the chassis 10 integrally supports the isolation unit 14 and the vapor phase decontaminant generator system 20 as a single unit. The isolation chamber 16 receives a load L, such as medical instruments, pharmaceutical containers, or any other similar load for decontamination. One or more biological indicators BI are positioned in association with the load L or otherwise distributed within the isolation chamber 16 for microbe kill verification. Optionally, a heater 29 is provided in the isolation chamber 16 to raise the temperature therein to reduce the potential for condensation.

The blower 24 includes an inlet 28 into which the carrier gas and the vapor phase decontaminant entrained therein is drawn. Preferably, the carrier gas/vapor phase decontaminant is communicated through a catalytic converter 30 which decomposes the $H_2O_2$ into its constituents—water and oxygen. In addition to blower speed, a butterfly valve 32 or the like controls the air flow rate (indicated by the arrows 34) through the recirculation ducting 36. As an alternative to recirculating the carrier gas through the duct system 36, it may simply be expelled to the atmosphere. To dry the carrier gas, a dryer 40 such as a desiccant is provided. Alternatively, the air dryer 40 can be provided by the heating, ventilation, and air-conditioning (HVAC) system of the facility in which the decontamination apparatus is located. In either case, the air is preferably conditioned such that it has a relative humidity of approximately 10% or less. The dried carrier gas is able to accept a greater amount of decontaminant vapor. Unlike conventional decontaminant vapor generation systems in which the desiccant needs to be periodically regenerated for several hours or more, the external air dryer 40 is adapted for continuous drying or the carrier gas. This allows the vaporizers 22 to be run continuously for increased decontamination and throughput efficiency.

Preferably, a carrier gas preheater 42 heats the carrier gas so that it can receive a greater concentration of decontaminant vapor. The carrier gas then passes through the one or more vaporizers 22. The vaporizers 22 generate decontaminate vapor, e.g., vapor phase $H_2O_2$ from aqueous $H_2O_2$ supplied from a canister 44 or other source, and saturate the carrier gas with the vapor phase decontaminant. The combined carrier gas/decontaminant vapor (indicated by the arrows 46) is drawn into the isolation chamber 16 through vaporizer outlets 48. The one or more vaporizers 22 are preferably of the type that dispense a precise amount of aqueous $H_2O_2$ in the form of droplets or mist onto a heated surface or the like such that the aqueous $H_2O_2$ is vaporized without being broken down. A metering pump or a scale system can be utilized to ensure the precise dispensing of aqueous $H_2O_2$.

The electronic control system 26 of the vapor phase decontaminant generation system 20 includes a central processing unit 50 which is preferably provided by one or more programmable logic controllers (PLC's) or other microcontrollers that control the operation of the decontaminant vapor generation system 20, including the blower 24, the butterfly valve 32, and the preheater 42. The processing unit 50 can also control any automated processing carried out within the isolation chamber 16. The electronic control system 26 is connected to the one or more vaporizers 22 through electrical connections 52 so that the control system 26 is able to control the operation of each vaporizer 22. Additionally, the control system 26 controls the operation of the optional heater 29 positioned within the isolation chamber 16.

Preferably, a plurality of decontamination process parameter sensors 54 provide input data 56 to the processing unit 50 of the electronic control system 26 such that the control system 26 can alter the decontamination process accordingly. For example, the sensors 54 preferably include one or more temperature sensors, one or more relative humidity sensors. and one or more sterilant concentration sensors. While the sensors 54 directly monitor the relevant parameters, the same and other parameters can be indirectly determined by the processing unit 50 in response to data regarding aqueous sterilant usage, air flow, and the like.

The control system 26 includes a visual display 60 for visual output of process parameters and other data to an operator of the decontamination apparatus. The visual display 60 can be provided by any suitable display such as a liquid crystal display, a vacuum fluorescent display, a light emitting diode display, or a cathode ray tube display. One or more operator input devices 62 are also provided for operator input of process parameters, security codes, and for operator control of the operation of the decontamination apparatus. The input devices 62 can include a keyboard, a keypad, a touch screen, knobs and switches, or any other suitable input devices. The control system further includes a printer 64 such as a laser, thermal, or impact printer that provides a hard copy output of decontamination process parameters including the time, date, the length of a decontamination cycle, decontaminant concentration, temperature, type of load L, and other such parameters of a decontamination operation.

Figure 3:
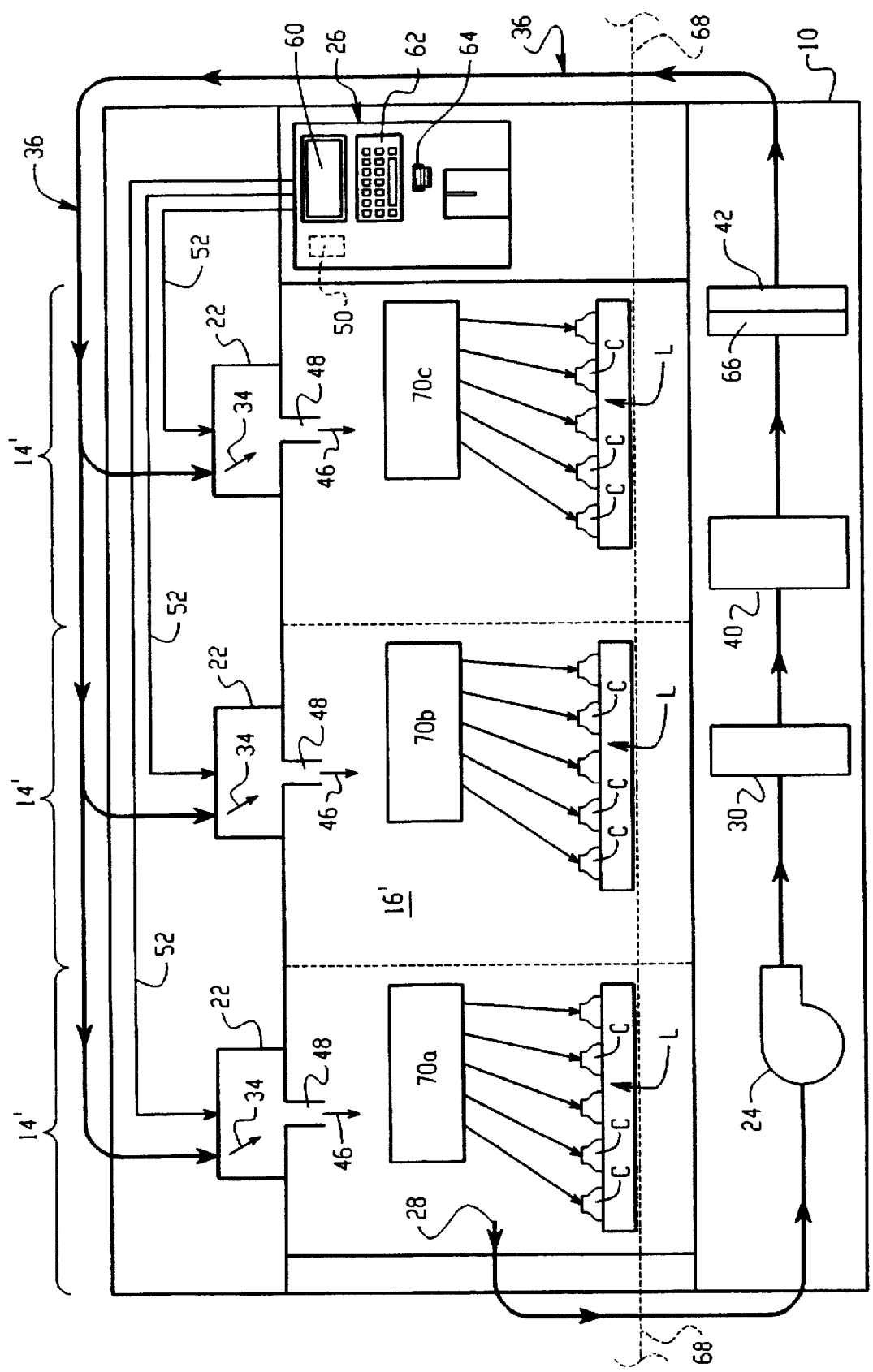

FIG. 3 illustrates an alternative embodiment of a decontamination apparatus in accordance with the present invention. For ease of comprehension, like components are indicated with like reference numerals. Related components are illustrated with like reference numerals including a primed (') suffix and new components are noted with new numerals. A plurality of rigid-walled isolator units 14' are interconnected to form a single isolation chamber 16'. Each isolator unit 14' preferably includes an integral decontaminant vaporizer 22. Alternatively, a single vaporizer 22 is utilized for the entire isolation chamber 16' or a small plurality of vaporizers 22 are positioned at strategic points around the chamber 16'. Each vaporizer 22 is connected to and controlled by the control system 26 through an electrical connection 52.

A blower 24 withdraws the carrier gas/decontaminant vapor through the blower inlet 28 and passes the same through the catalytic converter 30 and the air dryer 40, such as the external desiccant or HVAC system described above. An air filter 66 filters the carrier gas and the preheater 42 warms the carrier gas. The recirculation duct system 36 communicates the carrier gas to the one or more vaporizers 22 where it is combined with the decontaminant vapor and introduced into the isolation chamber 16' through the outlets 48 as indicated by the arrows 46.

The decontamination apparatus illustrated in FIG. 3 includes a conveyor system 68 that conveys one or more loads L individually or simultaneously into the isolation chamber 16'. The illustrated decontamination apparatus includes automated or semi-automated filling systems 70a, 70b, 70c that first sterilize and then aseptically fill and seal containers C of the load L. Preferably, the filling systems 70a–70c are controlled by the control system 26. For example, the containers C can be syringes, ampules, intravenous bags, or the like that must be filled in a sterile environment. Operator manipulation of the containers C or the filling systems 70a–70c is provided, if needed, through glove boxes or the like. When the containers C are filled and sealed, they are discharged from the isolation chamber 16'.

The invention has been described with reference to the preferred embodiments. Obviously, modifications and alterations will occur to others upon reading and understanding the preceding specification. It is intended that the invention be construed as including all such modifications and alterations insofar as they come within the scope of the appended claims or the equivalents thereof.

Having thus described the preferred embodiments, the invention is now claimed to be:

1. A decontamination apparatus comprising:

a chassis supported on a floor;

a plurality of individual modular isolator units each connected to and supported by said chassis, said plurality of modular isolator units interconnected to define a generally hollow closed isolation chamber for receiving and containing a load to be microbially decontaminated;

a plurality of vapor phase decontaminant generation systems, each of said plurality of individual modular isolator units including at least one of said vapor phase decontaminant generation systems permanently integrated therewith, such that upon interconnection of said plurality of individual modular isolation units to define said isolation chamber, said plurality of vapor phase decontaminant generation systems are operatively connected and together supply vapor phase decontaminant uniformly throughout said isolation chamber, each of said vapor phase decontaminant generator systems including a carrier gas inlet, an outlet in fluid communication with said isolation chamber, and at least one vaporizer for vaporizing aqueous decontaminant by dispensing a metered amount of aqueous decontaminant onto a heated surface to vaporize said aqueous decontaminant into a vapor phase decontaminant;

a blower including an inlet in fluid communication with said generally hollow isolation chamber and an outlet, said blower drawing a carrier gas into said isolation chamber through each of said vapor phase decontaminant generation systems such that said vapor phase decontaminant generated by each of said generator systems is entrained into said carrier gas and drawn into said isolation chamber;

a continuously operable air dryer in fluid communication with said inlet of each of said plurality of vapor phase decontaminant generation systems for reducing the humidity of said carrier gas prior to said carrier gas passing through said plurality of vapor phase decontaminant generation systems;

a carrier gas preheater in fluid communication with said inlet of each of said plurality of vapor phase decontaminant generation systems to heat said carrier gas to a select temperature prior to said carrier gas entering each of said plurality of vapor phase decontaminant generation systems; and, an electronic control system including at least one central processing unit operatively connected to said blower, each of said vapor phase decontaminant generation systems, and said carrier gas preheater to control operation of each vaporizer, said blower, and said preheater to vary the concentration of vapor phase decontaminant entrained into said carrier gas and to control the flow and temperature of said carrier gas in said isolation chamber.

2. The decontamination apparatus as set forth in claim 1 wherein the electronic control system individually controls the vapor phase decontaminant generator systems to distribute vapor phase decontaminant uniformly throughout the volume of said isolation chamber collectively defined by said modules.

3. The decontamination apparatus as set forth in claim 1 wherein said at least one of said vapor phase decontaminant generator systems integrally connected with each of said plurality of modular isolator units is housed in an upper portion of said modular isolator unit such that when said plurality of modular isolator units are connected to define said generally hollow isolation chamber, each of said plurality of vapor phase decontaminant generator systems is positioned above a different region of said hollow isolation chamber for uniform distribution of vapor phase decontaminant throughout said isolation chamber.

4. The decontamination apparatus as set forth in claim 1 further comprising an automated container filling system housed within the generally hollow isolation chamber for aseptic container filling operations.

5. The decontamination apparatus as set forth in claim 4 further comprising a conveyor system for conveying a load of containers into and out of said generally hollow isolation chamber.

6. The decontamination apparatus as set forth in claim 1 wherein said integral vapor phase decontaminant generator system further includes a catalytic converter for decomposing vaporized decontaminant evacuated, from said generally hollow isolation chamber.

7. The decontamination apparatus as set forth in claim 6 further comprising:

a carrier gas filter positioned in fluid communication with each of said plurality of vapor phase decontaminant generator systems for filtering said carrier gas prior to passage of said carrier gas through said vaporizer of each of said decontaminant generator systems.

8. A decontamination apparatus comprising:

a chassis supported on a support surface;

a plurality of individual modular isolator units each connected to and supported by said chassis, said plurality of modular isolator units interconnected to define a generally hollow closed isolation chamber for receiving and containing a load to be microbially decontaminated;

a plurality of vapor phase decontaminant generation systems, said plurality of vapor phase decontaminant generation systems being operatively connected to supply vapor phase decontaminant uniformly throughout said isolation chamber, each of said vapor phase decontaminant generator systems including:

a carrier gas inlet connected to an external heating, ventilation, and air-conditioning system, an outlet in fluid communication with said isolation chamber, and at least one vaporizer for vaporizing aqueous decontaminant by dispensing a metered amount of aqueous decontaminant onto a heated surface to vaporize said aqueous decontaminant into a vapor phase decontaminant;

a blower including an inlet in fluid communication with said generally hollow isolation chamber and an outlet, said blower drawing a carrier gas from said heating, ventilation, and air-conditioning system into said isolation chamber through each of said vapor phase decontaminant generation systems such that said vapor phase decontaminant generated by each of said generator systems is entrained into said carrier gas and drawn into said isolation chamber, said blower outlet being connected in fluid communication to said heating, ventilation, air-conditioning system for continuous conditioning of carrier gas evacuated from said isolation chamber;

an electronic control system including at least one central processing unit operatively connected to said blower and each of said vapor phase decontaminant generation systems to control operation of each vaporizer individually and said blower to vary the concentration of vapor phase decontaminant entrained into said carrier gas by each vaporizer and to control the flow of said carrier gas through said isolation chamber; and, at least one vapor phase decontamination process parameter sensor positioned in said isolation chamber and operatively connected to said electronic control system such that said electronic control system varies at least one of the flow rate of carrier gas through said isolation chamber and the operation of said plurality of vapor phase decontaminant generator systems in response to data received from said at least one sensor.

9. A decontamination apparatus comprising:

a plurality of isolator unit modules connected together to define an elongated hollow isolation chamber, isolator units being mounted to a central portion of a chassis such that the chassis defines open regions above and below the isolator modules;

a plurality of decontaminant vapor generators mounted in the open region of the chassis above the isolator modules to generate and discharge decontaminant vapor downward into a plurality of regions of the isolation chamber;

at least one blower mounted in the open regions above and below the isolator modules for circulating a carrier gas through the vapor generators entraining the generated decontaminant vapor and circulating the carrier gas and entrained decontaminant vapor along the isolation chamber;

at least one filter mounted in the open regions above and below the isolator modules for removing contaminants from the circulated carrier gas;

at least one dryer mounted in the open regions above and below the isolator modules for reducing humidity of the carrier gas before the carrier gas is circulated through the vapor generator;

a key pad mounted on the chassis for inputting control instructions;

a central control unit mounted on the chassis and connected with the operator input device, the at least one blower, and the plurality of vapor generators to control decontaminant vapor concentration in each of the plurality of isolation chamber regions and circulation of the carrier gas and entrained decontaminant vapor along the elongated isolation chamber.

10. The decontamination apparatus as set forth in claim 8 further comprising an automated container filling system housed within the generally hollow isolation chamber for aseptic container filling operations.

11. The decontamination apparatus as set forth in claim 10 further comprising a conveyor system for conveying a load of containers into and out of said generally hollow decontamination chamber.

12. The decontamination apparatus as set forth in claim 8 further comprising at least one catalytic converter in fluid communication with said blower for decomposing vaporized decontaminant evacuated from said generally hollow isolation chamber.

13. The decontamination apparatus as set forth in claim 8 further comprising a carrier gas filter in fluid communication with each of said plurality of vapor phase decontaminant generation systems for filtering said carrier gas prior to said carrier gas passing through said plurality of decontaminant generations systems.

* * * * *